(12) United States Patent
Hartley et al.

(10) Patent No.: US 9,101,456 B2
(45) Date of Patent: Aug. 11, 2015

(54) THORACIC AORTA STENT GRAFT WITH ACCESS REGION

(75) Inventors: David E Hartley, Wannanup (AU); Roy K. Greenberg, Bratenahl, OH (US); Krasnodar Ivancev, Camden (GB); Michael Lawrence-Brown, City Beach (AU)

(73) Assignees: COOK MEDICAL TECHNOLOGIES LLC, Bloomington, IN (US); THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 13/061,065
(22) PCT Filed: Aug. 25, 2009
(86) PCT No.: PCT/US2009/004827
§ 371 (c)(1),
(2), (4) Date: Jul. 1, 2011
(87) PCT Pub. No.: WO2010/024879
PCT Pub. Date: Mar. 4, 2010

(65) Prior Publication Data
US 2011/0257731 A1 Oct. 20, 2011

Related U.S. Application Data

(60) Provisional application No. 61/190,141, filed on Aug. 26, 2008.

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/061* (2013.01); *A61F 2002/067* (2013.01); *A61F 2002/075* (2013.01); *A61F 2250/0039* (2013.01)

(58) Field of Classification Search
CPC ..... A61F 2/07; A61F 2/856; A61F 2002/061; A61F 2002/065; A61F 2002/067; A61F 2002/828
USPC ........................ 623/1.13, 1.35, 1.27, 1.3–1.31
See application file for complete search history.

(56) References Cited

U.S. PATENT DOCUMENTS 6,814,752 B1   11/2004   Chuter
2003/0088305 A1   5/2003   Van Schie et al.
(Continued)

FOREIGN PATENT DOCUMENTS

EP   1245202   10/2002
JP   04231954   8/1992
(Continued)

OTHER PUBLICATIONS

International Search Report and Written Opinion for PCT/US2009/004827 dated Nov. 9, 2009, 16 pgs.
(Continued)

*Primary Examiner* — Howie Matthews
(74) *Attorney, Agent, or Firm* — Brinks Gilson & Lione

(57) ABSTRACT

A stent graft (2) for placement in the thoracic arch of a patient has a first tubular body portion (6) with a first lumen therein for placement in the ascending aorta of a patient and a second tubular body portion (8) to extend along the thoracic arch and down the descending aorta. The second tubular body portion is of a lesser diameter than the first tubular body portion. There is a step portion (10) between the first body portion and the second body portion. The step portion is joined to and continuous with the first portion and the second portion. A first side of each of the first body portion, the step portion and the second body portion are substantially aligned so that there is a step (18) defined on a second side opposite to the first side of the body portion. There is an aperture (30) in the step portion and an internal tube (32) extending from the aperture towards the first body portion. The internal tube is divided along part of its length into at least two smaller internal tubes (34, 36) with the smaller internal tubes opening into the first lumen.

10 Claims, 6 Drawing Sheets

(56) References Cited

U.S. PATENT DOCUMENTS

| | | | |
|---|---|---|---|
| 2003/0199967 A1 | 10/2003 | Hartley et al. | |
| 2006/0184228 A1 | 8/2006 | Khoury | |
| 2009/0048663 A1 | 2/2009 | Greenberg | |
| 2009/0319022 A1* | 12/2009 | Hartley et al. | 623/1.13 |

FOREIGN PATENT DOCUMENTS

| | | |
|---|---|---|
| JP | 2004298548 | 10/2004 |
| JP | 2005521471 | 7/2005 |
| WO | WO2005/032340 | 4/2005 |
| WO | WO2008/021557 | 2/2008 |
| WO | WO2009/020653 | 2/2009 |

OTHER PUBLICATIONS

Patent Examination Report No. 1 for Australian Patent Application No. 2009286062 dated Feb. 25, 2013, 3 pgs.
Patent Examination Report for European Patent Application No. 09789202.0 dated Dec. 14, 2012, 5 pgs.
Patent Examination Report for European Patent Application No. 09789202.0 dated Aug. 5, 2014, 4 pgs.
Request for Change of Applicant for Japanese Patent Application No. 2011-524987 filed Sep. 14, 2012, 6 pgs.
Office Action for Japanese Patent Application No. 2011-524987 dated Aug. 14, 2013, 5 pgs. including English translation, 5 pgs.
Present claims (marked-up and clean version) for Japanese Patent Application No. 2011-524987 in English, 4 pgs.
International Preliminary Report on Patentability for PCT/US2009/004827 dated Mar. 10, 2011, 9 pgs.
Office Action for European Patent Application No. 09 789 202.0 dated May 28, 2015, 4 pages.

* cited by examiner

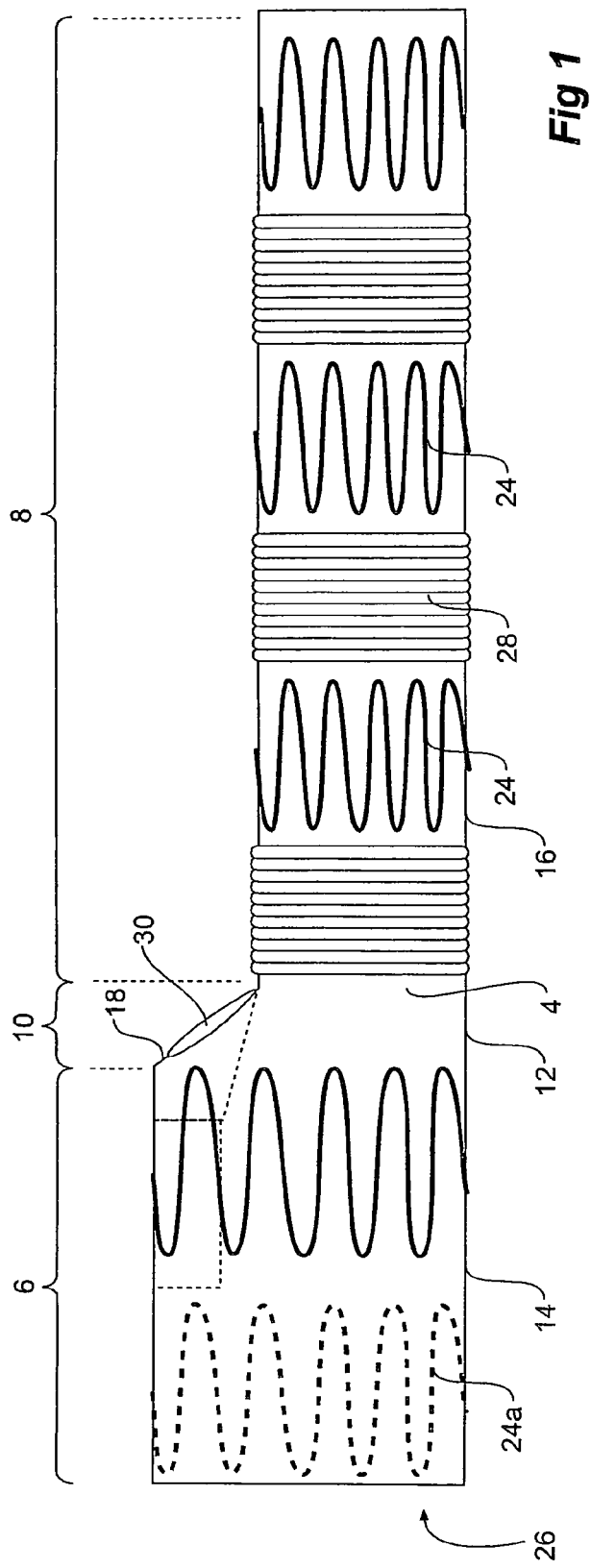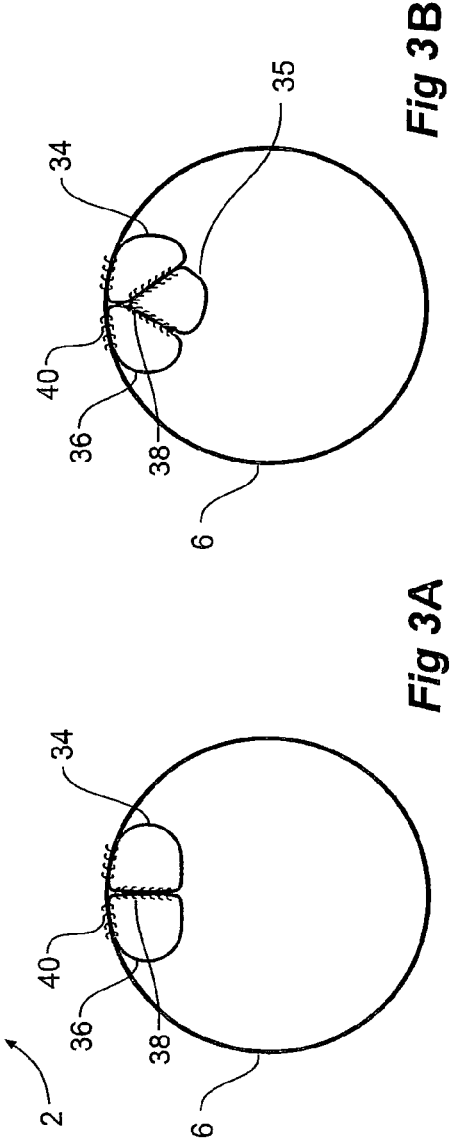

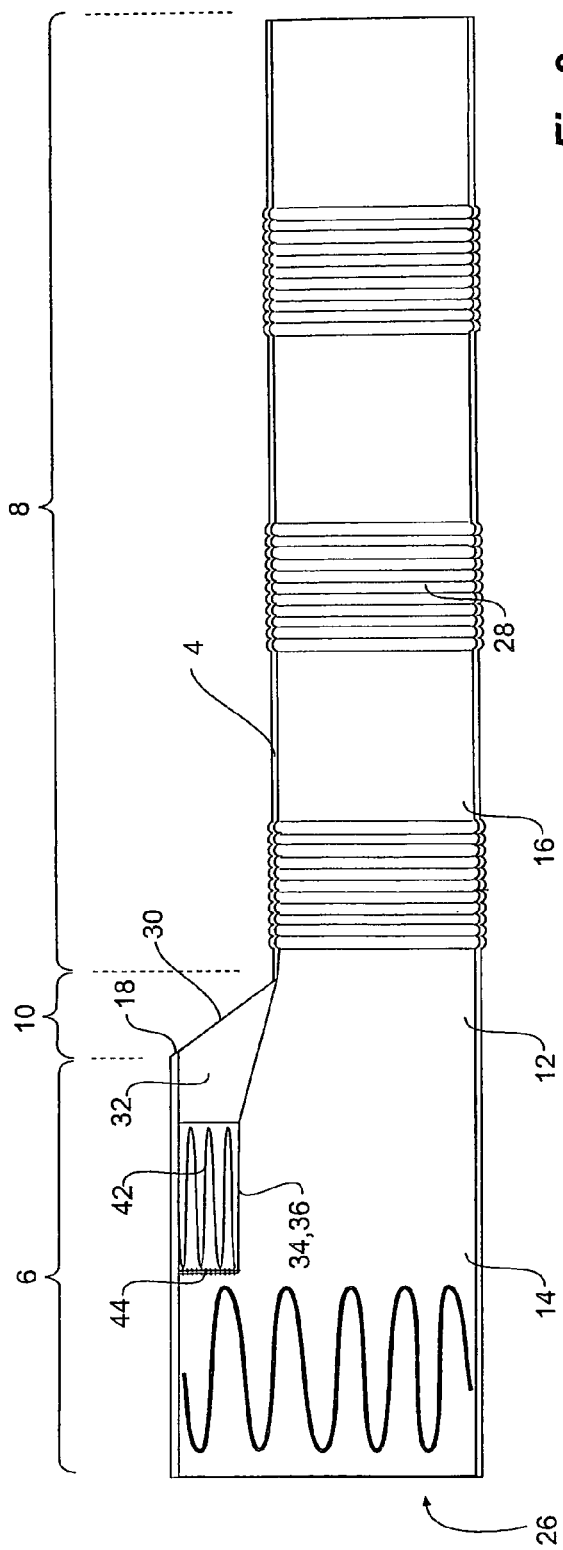
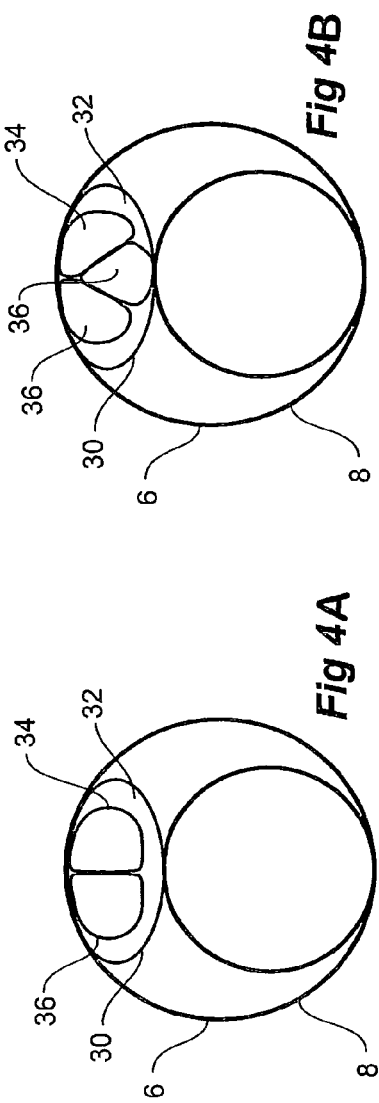

THORACIC AORTA STENT GRAFT WITH ACCESS REGION

RELATED APPLICATIONS

The present patent document is a §371 filing based on PCT Application Serial No. PCT/US2009/004827, filed Aug. 25, 2009 (and published as WO 2010/024879A1 on Mar. 4, 2010), designating the United States and published in English, which claims the benefit of the filing date under 35 U.S.C. §119(e) of Provisional U.S. Patent Application Ser. No. 61/190,141, filed Aug. 26, 2008. All of the foregoing applications are hereby incorporated by reference in their entirety.

TECHNICAL FIELD

This invention relates to a medical device for treatment of aortic arch disease and more particularly to a stent graft for deployment into the thoracic aorta of a patient for that purpose.

BACKGROUND ART

In recent years endovascular implantable devices have been developed for treatment of aortic aneurysms. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system whereafter the delivery system is inserted into the vascular system of the patient such as through a femoral incision. The leading end of the delivery system is manoeuvred to the treatment site over a previously positioned guide wire. Through manipulation of a control system that extends to the proximal end of the catheter from the distal end of the system outside the patient, the implantable device is deployed by holding the device at its location and withdrawing a surrounding sheath. The implantable device or stent graft can then self expand or be expanded through the use of a balloon which is introduced with a stent graft introduction device. The stent graft becomes anchored into position in healthy wall tissue of the aorta, by barbs for example. The delivery system is then removed leaving the inflatable device in position to reverse an aneurysm in the aorta in a manner that channels all blood flow through the stent graft so that no blood flow enters the aneurysm. As a result, not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian. For treatment of an aneurysm in the region of the thoracic arch provision must be made for blood supply to continue to these arteries. For this purpose fenestrations are provided into the wall of a stent graft in that region. Access is generally obtained to these fenestrations, to deploy side arms into the stent graft, via the left or right brachial arteries or less commonly via the left or right carotid arteries. Once into the thoracic arch via such an artery the fenestration in the stent graft must be catheterised. To simplify this, it is desirable to have some working space in the outer side of the thoracic arch which is the region that the branch vessels enter the arch.

It is the object of this invention to provide an arrangement of stent graft to overcome the above problem or to at least provide the practitioner with a useful alternative.

Throughout this specification the term distal with respect to a portion of the aorta, a deployment device or a prosthesis such as a stent graft is intended to mean the end of the aorta, deployment device or prosthesis such as a stent graft further away in the direction of blood flow from the heart and the term proximal is intended to mean the portion of the aorta, deployment device or end of the prosthesis nearer to the heart. For other lumens within the human or animal body the terms caudal and cranial respectively should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

DISCLOSURE OF THE INVENTION

According to a first aspect of the present invention, there is provided a stent graft for placement in the thoracic arch of a patient, the stent graft comprising a first tubular body portion and a second tubular body portion, the second tubular body portion having a smaller diameter than the first tubular body portion, the second tubular body portion having at least one aperture for receiving a side branch stent graft such that when the stent graft is curved during deployment, the at least one aperture is located on or adjacent the outside of the curve.

It will be seen that by this invention there is provided a stent graft for placement in the thoracic arch of a patient. In use, the first body portion is placed in the ascending aorta of a patient and the second body portion extends around the thoracic arch and down the descending aorta. The stent graft can be placed such that the portion of the graft where the diameter starts to reduce is just proximal of the brachiocephalic artery and on the outside of the curve of the thoracic arch. By this placement there is defined, by the difference in diameter of the first and second portions, an open region outside the stent graft. This open region is distal of the aperture in the second portion, so that blood flow can occur through the aperture to the open region enabling circulation to be preserved to the major vessels through the internal branches during the progress of an operation. As the more distal second portion of the stent graft is of a lesser diameter there is provided a working space in which a guide wire from the branch arteries can be directed to enter the aperture to enable catheterisation. Subsequently a side branch stent graft can be deployed from the respective branch artery into the stent graft to provide blood flow into that branch artery.

In one example, a stent graft with a single aperture in the region of reduced diameter could take a leg extension for one great artery with surgical bypasses to the other arteries. The aperture (or fenestration) may be in a leading face of the reduced diameter region or hollow.

The stent graft may further comprise an internal tube extending from the aperture towards the first body portion.

The internal tube may be divided along at least part of its length into at least two smaller internal tubes opening into the lumen of the first body portion.

The two discrete tubes allow leg extensions for two great arteries.

The internal tube may be divided along part of its length into three smaller internal tubes which open into the lumen of the first body portion.

During an operation, this arrangement permits a working space in which a guide wire from one of the branch arteries can be directed to enter the internal tube and subsequently one of the smaller internal tubes to enable catheterisation.

In a further aspect of the present invention, there is provided a stent graft for placement in the thoracic arch of a patient, the stent graft comprising a first tubular body portion with a first lumen therein for placement in the ascending aorta of a patient and a second tubular body portion to extend around the thoracic arch and down the descending aorta, the second tubular body portion being of a lesser diameter than the first tubular body portion, a step portion between the first body portion and the second body portion, the step portion being joined to and continuous with the first portion and the second portion, a first side of the first body portion, a first side of the step portion and a first side the second body portion being substantially aligned such that a step is defined on a second side opposite to the first side of the body portion, an aperture in the step portion and an internal tube extending from the aperture towards the first body portion, the internal tube being divided along part of its length into at least two smaller internal tubes, the at least two smaller internal tubes opening into the first lumen.

At least one of the first tubular body portion and the second tubular body portion comprise stents therealong. Preferably each of the tubular body portions comprise stents therealong. Preferably the stents comprise self expanding stents for example zig zag self expanding stents. The plurality of self expanding stents can be spaced apart longitudinally by substantially the axial length of adjacent stents to allow for flexibility of the stent graft. The graft material between the stents can be corrugated to allow for flexibility of the stent graft.

The stent graft can be formed into a pre-curved shape longitudinally defined by an inside curved side and an outside curved side and such that the second side is on the outside curved side. In this case, the aperture in the step portion is on the outside of the curve.

In a preferred embodiment, the aperture in the step portion or reduced diameter region can be placed to one side of the outside of the curve. In this case, the aperture is adjacent or offset from the outside of the curve.

Typically, the first tubular body portion can have a diameter of from 35 to 50 mm. The second tubular body portion can have a diameter of from 20 to 30 mm. The step portion can have a width of from 10 to 30 mm. The internal tube can be substantially circular or oval in cross section. The internal tube may have a diameter of from 15 to 20 mm. Where there are two smaller internal tubes the two smaller internal tubes can have diameters of 10 mm and 12 mm respectively in one example.

Preferably there are two smaller internal tubes. There may be three smaller internal tubes, one for each of the great vessels of the thoracic arch.

In a further embodiment the smaller internal tubes each have a diameter in the range of from 6 to 10 mm. In an alternative embodiment one of the two smaller internal tubes has a diameter in the range of from 6 to 8 mm and the other of the two smaller internal tubes has a diameter in the range of from 8 to 12 mm. In such a situation the larger of the two smaller internal tubes is preferably adjacent the wall of the first portion.

According to a further aspect of the invention, there is provided a method of treatment of aortic aneurysm comprising deploying a stent graft as claimed in any of claims 1 to 28 into the thoracic arch such that the aperture is placed just proximal of the junction of the aorta with the brachiocephalic artery.

According to a further aspect of the invention, there is provided a method of treatment of aortic aneurysm comprising deploying a stent graft as claimed in of claims 2 to 28 into the thoracic arch such that the step portion is just proximal of the junction of the aorta with the brachiocephalic artery.

BRIEF DESCRIPTION OF THE DRAWINGS

Preferred embodiments of the invention will now be described with reference to the accompanying drawings.

FIG. 1 shows a side view of a first embodiment of stent graft according to the present invention;

FIG. 2 shows a longitudinal cross sectional view of the embodiment shown in FIG. 1;

FIG. 3A shows a view from the proximal end of the embodiment shown in FIG. 1;

FIG. 3B shows a view from the proximal end of an alternative embodiment of the invention;

FIG. 4A shows a view from the distal end of the embodiment shown in FIG. 3A;

FIG. 4B shows a view from the distal end of the embodiment shown in FIG. 1;

DESCRIPTION OF THE PREFERRED EMBODIMENTS

Figure 5:
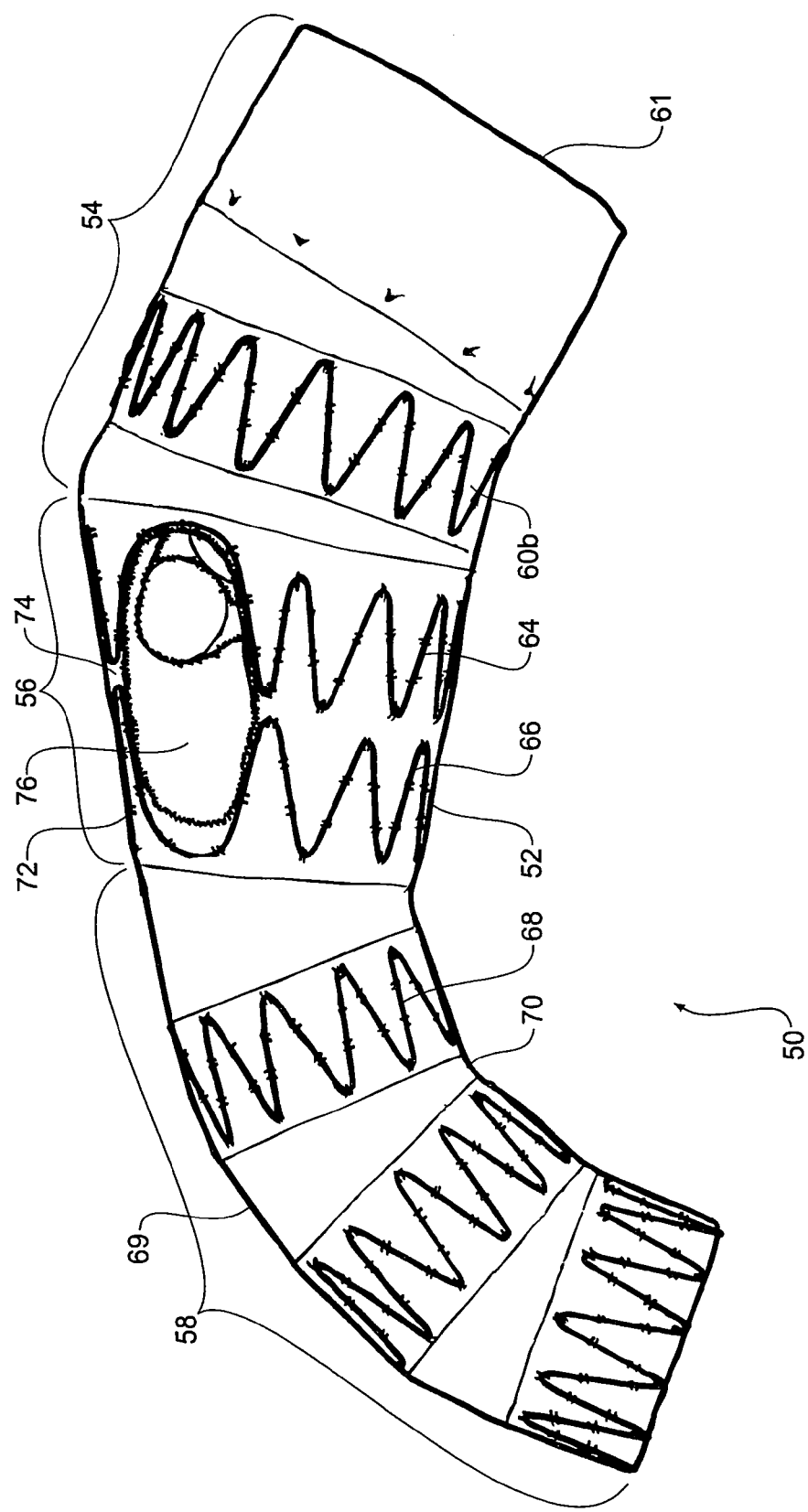
FIG. 5 shows an alternative embodiment of stent graft according to the present invention.

Now looking more closely at the drawings and more particularly the embodiment shown in FIGS. 1 to 4 it will be seen that the stent graft 2 comprises generally a tubular body 4 of a biocompatible graft material such as Dacron. The tubular body can be considered as comprising three main portions, a first portion 6, a second portion 8 and a step portion 10 between the first portion and the second portion. The first portion 6 is of a diameter to fit into and engage the walls of the ascending aorta of a patient. The first portion may have a diameter of from 35 to 50 mm. The second portion 8 is of a lesser diameter than the first portion by 5 to 15 mm. The length of the first portion may be from 20 to 60 mm, the length of the second portion may be from 80 to 150 mm and the step portion may have a length of from 10 to 30 mm. The step portion 10 comprises a substantially straight inner side 12 aligned with inner sides 14 and 16 of the first and second portions respectively. The step portion 10 comprises an angled or tapered outer side 18 which extends from the outer side 20 of the first portion to the outside 22 of the second portion.

A plurality of zig-zag stents 24 provide support for the tubular body along the length thereof. At the proximal end 26 of the stent graft the zig-zag stent 24*a* is on the inside to provide a smooth outer sealing surface to engage against the wall of the ascending aorta. Particularly in the second portion 8 the stents are spaced apart to enable flexibility of the stent graft to conform to the shape of the thoracic arch and the descending aorta. The stents in this region may be spaced apart by substantially the axial length of adjacent stents. In this embodiment the graft material in the spaces between the stents is formed into a corrugated structure 28 to give good flexibility between the stents as well as providing structural rigidity. The graft material in the spaces between the stents can be reinforced with a helical reinforcement wire. Helical reinforcement for graft material is shown in U.S. patent application Ser. No. 12/261,860 entitled "Flexible Stent Graft" and the teachings therein are incorporated herein in their entirety.

In the step portion 10 an aperture 30 is formed with an internal tube 32 extending from the aperture towards the proximal end 26 of the stent graft. A short distance within the recess from the aperture the internal tube divides into two smaller tubes 34 and 36 which again extend from the internal tube 32 towards the proximal end 26 of the stent graft.

In use when the stent graft is placed into the thoracic arch of a patient the step portion is positioned just proximal of the brachiocephalic artery and on the outside of the curve of the thoracic arch. The first portion 6 extends proximally into the ascending aorta and the second portion 8 extending distally into the descending aorta. There is defined, by the difference in diameter of the first and second portions, an open region defined between the stent graft and the outer side of the thoracic arch distal of the aperture in the step portion 10, so that circulation is preserved to the major vessels through the internal branches during the progress of an operation. As the more distal second portion of the stent graft is of a lesser diameter the open region provides a working space in which a guide wire from the major branch arteries can be manipulated to be directed to enter the aperture 30 and the internal tube 32 and subsequently one of the smaller internal tubes 34 and 36 to enable catheterisation. Subsequently a side branch stent graft can be deployed from the respective branch artery into one of the smaller tubes to provide blood flow into that branch artery.

As can be seen in FIG. 3A which is a view from the proximal end 26 of the stent graft the smaller tubes 34 and 36 have their proximal ends formed into opposed D shapes and the uprights of each of the D's are joined to each other 38 to ensure that there are no dead zones in the stent graft in use. The smaller tubes 34 and 36 are also joined to the side wall of the first portion at 40. FIG. 4A shows the stent graft from the distal end. It can be particularly seen that the internal tube 32 reduces to two smaller tubes 34 and 36.

Each of the smaller tubes 34 and 36 are also supported along their length with a zig-zag stent 42 and are reinforced at their proximal ends with a reinforcing ring 44.

FIGS. 3B and 4B show views from the proximal end and distal end respectively of an alternative embodiment of the invention. In this embodiment there are three smaller internal tubes 34, 35, 36 extending from the internal tube 32 and directed towards the proximal end of the stent graft. Each of the brachiocephalic, the left carotid and the left subclavian can be connected to one of the smaller tubes via respective branch grafts.

Figure 6:
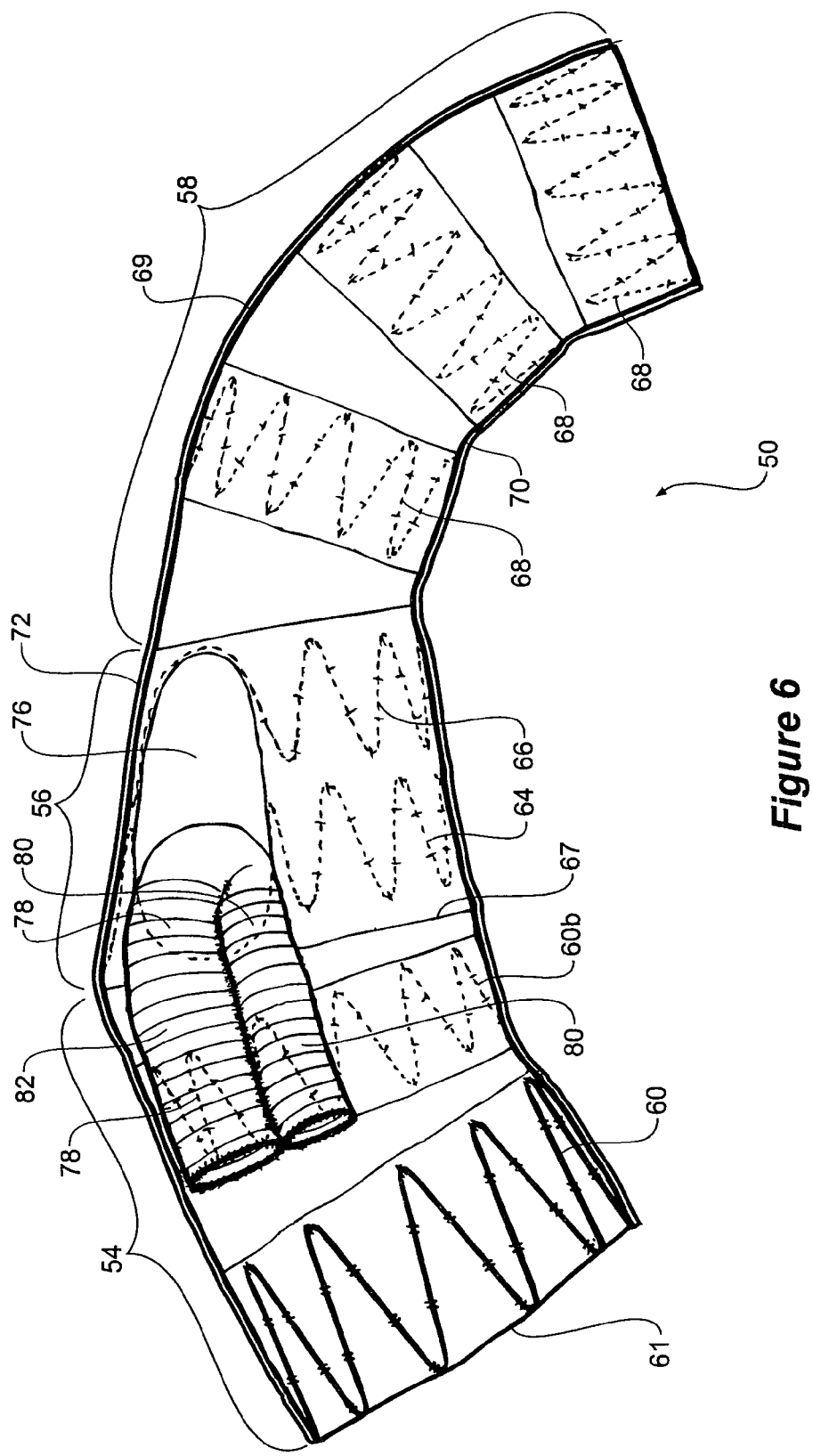
FIG. 6 shows a longitudinal cross sectional view of the embodiment shown in FIG. 5.
Figure 7:
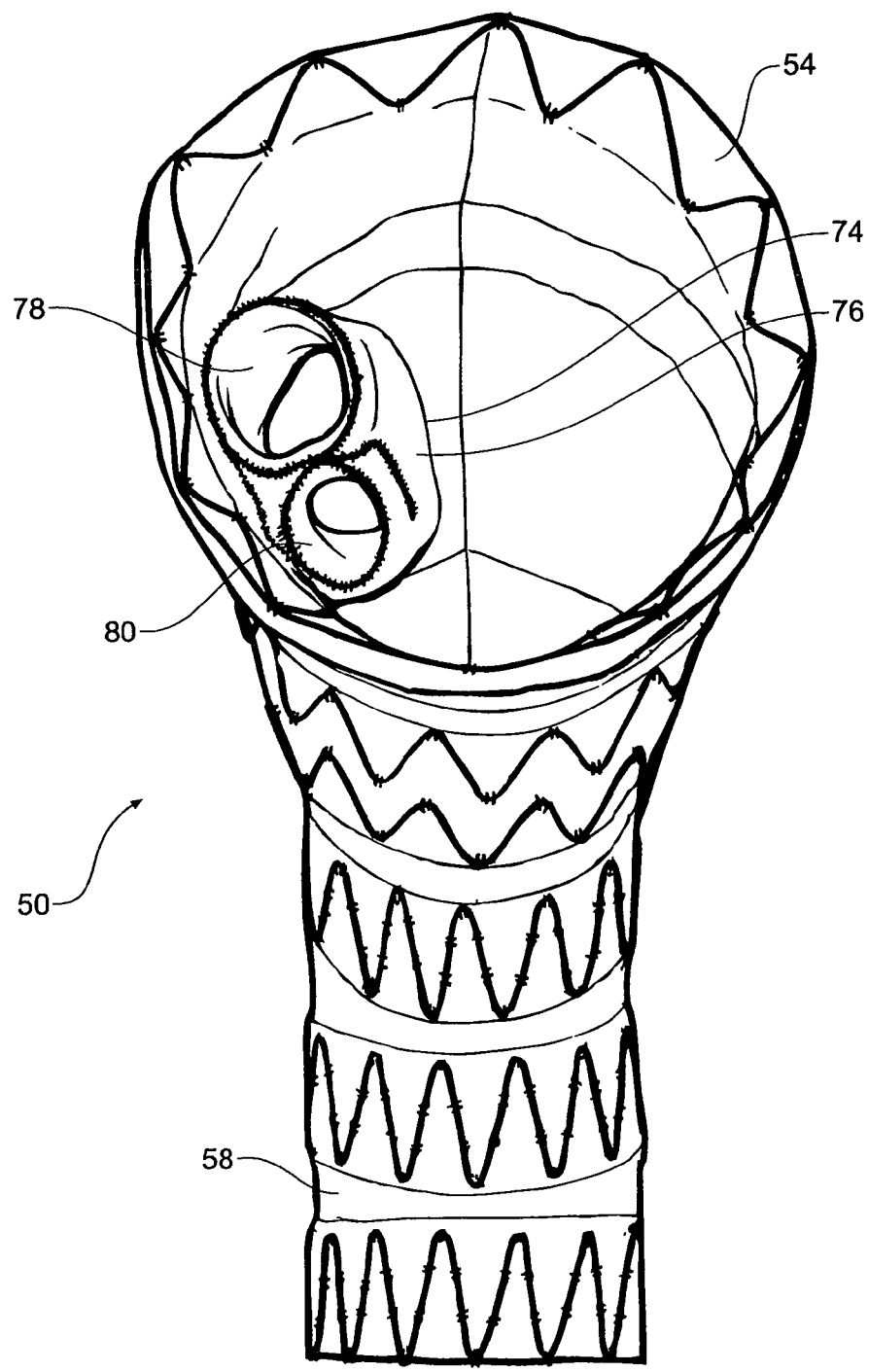
FIG. 7 shows a view from the proximal end of the embodiment shown in FIG. 1.

FIGS. 5 to 7 show an alternative embodiment of stent graft according to the present invention. In this embodiment the tubular body 52 of this embodiment of stent graft 50 comprises a first portion 54, a step portion 56 and a second portion 58.

The first portion 54 comprises a tubular body of a biocompatible graft material and is supported by self expanding zig-zag stents 60. The stent 60a at the proximal end is internal to provide a smooth sealing surface to engage against the wall of the ascending aorta and the stent 60b is external. The first portion may have a diameter of from 35 to 50 mm.

The second portion 58 is again formed from a tubular body of a biocompatible graft material and is supported by self expanding zig-zag stents 68. The tubular body of the second portion is formed into a partly curved shape by a greater distance between the stents 68 on the outside of the curve 69 than the inside of the curve 70. The second portion 58 can have a diameter in the range of from 30 to 40 mm.

The step portion 56 is again formed from a frusto-conical tubular body of a biocompatible graft material and is supported by self expanding zig-zag stents 64 and 66. The step portion has a diameter at its proximal end 67 which is substantially the same as the diameter of the first portion and a diameter at its distal end which is substantially the same as the diameter of the second portion. The step portion has all of its taper between the diameter of the first portion and the diameter of the second portion on the outside 72 of the curve of the stent graft.

As can be particularly seen in FIG. 5 the step portion 56 has an aperture or fenestration 74 which opens into a recess 76 within the step portion and the recess extends proximally towards the first portion 54. The aperture is offset from the outside curve of the stent graft so that when it is positioned within the thoracic arch the aperture opens slightly to the ventral side of the arch. The great vessels, the brachiocephalic, the left carotid and the left subclavian, branch from the thoracic arch and are slightly ventral with respect to the thoracic arch.

The recess 76 within the step portion 56 opens at its proximal end into two tubes 78 and 80. Each of the tubes may be of the same diameter or the uppermost of the tubes 78 may have a diameter which is greater than the diameter of the lower tube 80. The tubes 78 and 80 extend towards the proximal end 61 of the stent graft 50.

Each of the smaller internal tubes 78 and 80 can be reinforced with a helical shape memory wire reinforcement 83. Helical reinforcement for graft material is shown in U.S. patent application Ser. No. 12/261,860 entitled "Flexible Stent Graft" and the teachings therein are incorporated herein in their entirety.

Figure 8:
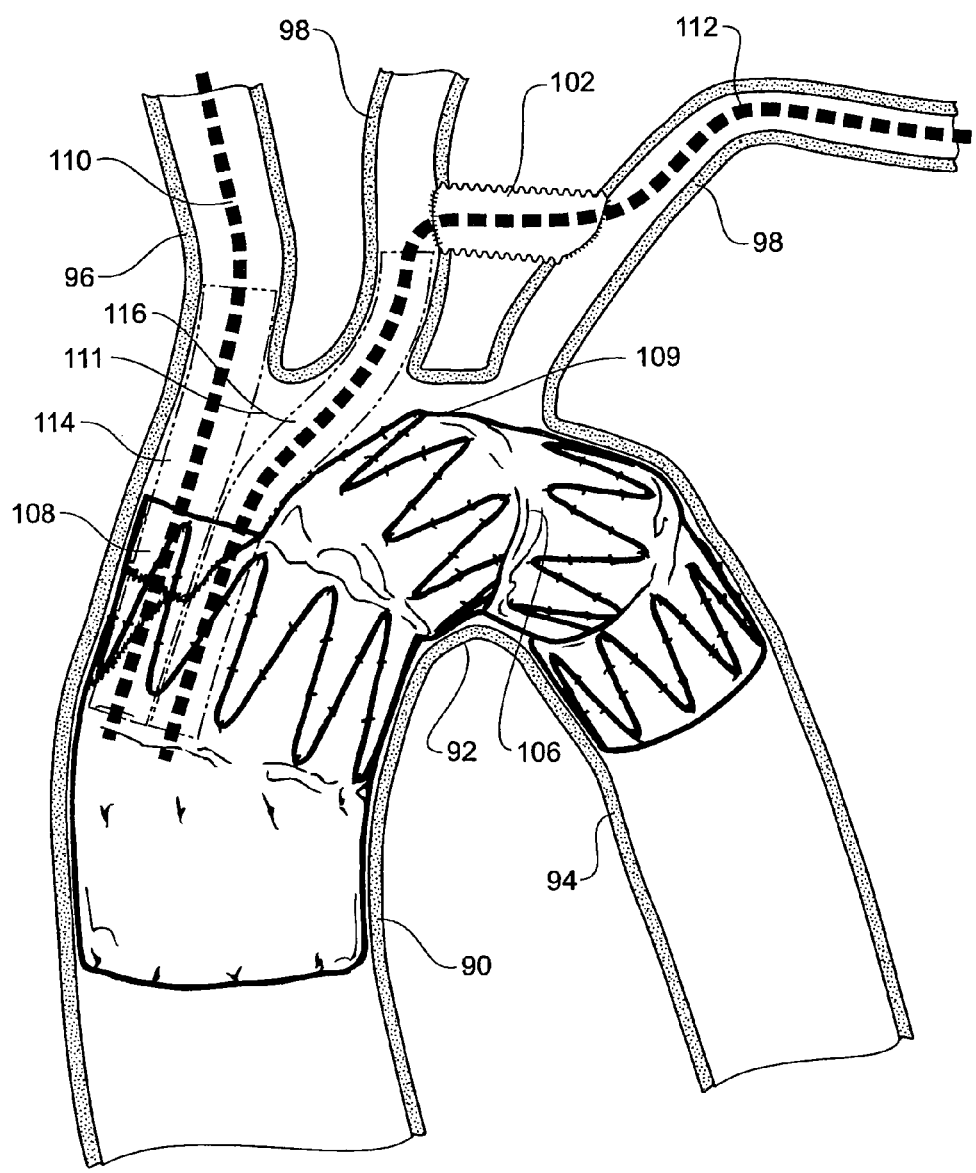
FIG. 8 shows a schematic view of the placement of a stent graft according to the present invention into the thoracic arch of a patient.

FIG. 8 shows a schematic view of the placement of a stent graft according to one embodiment of the present invention into the thoracic arch of a patient.

The thoracic arch shown schematically comprises an ascending aorta 90 extending to the thoracic arch 92 and a descending aorta 94 from the thoracic arch. Substantially at the top of the thoracic arch but slightly to the ventral side of the arch the major vessels branch off the arch. The major vessels are the brachiocephalic artery 96, the common or left carotid artery 98 and the left subclavian 100. In a preparatory operation an anastomosis 102 is provided between the common carotid artery 98 and the left subclavian 100. The anastomosis provides access between the common carotid artery 98 and the left subclavian artery 100 which enables endovascular access to the stent graft via brachial arteries in the left arm rather than endovascular access via the left carotid artery which may be more complex.

The stent graft 106 is deployed into the thoracic arch such that the step portion 108 is just proximal of the junction of the aorta with the brachiocephalic artery 96. This means that there is defined between the step portion, the upper wall of the thoracic arch and the second portion of the stent graft 109, an open region 111 so that circulation can be preserved to the major vessels through the internal tubes 78 and 80 and the recess 76 (see FIGS. 6 and 7) during the operation of deployment of the stent graft and subsequent placement of side branch grafts. The space also assists in enabling catheterisation of the internal tubes. A catheter can be inserted as shown by the dotted line 110 to enter the larger of the tubes 78 to enable placement of a side branch stent graft 114 for the brachiocephalic artery 96 and a catheter can be inserted as shown by the dotted line 112 to enter the smaller of the tubes 80 to enable placement of a side branch stent graft 116 for the common carotid artery 98 and the left subclavian artery 100.

Because the space 111 provides maintenance of circulation to the major vessels there may be circumstances where an operation can be carried out in stages.

In a preferred embodiment the larger of the internal tubes 78 has a diameter of 12 mm and the smaller of the tubes has a diameter of 10 mm.

Many modifications and other embodiments of the invention will come to the mind of one skilled in the art having the benefit of the teachings presented in the foregoing descriptions and associated drawings. Therefore, it is understood that the invention is not to be limited to the specific embodiments disclosed, and that modifications and embodiments are intended to be included within the scope of the appended claims.

The invention claimed is:

1. A stent graft for placement in the thoracic arch of a patient, the stent graft comprising a first tubular body portion, a second tubular body portion, and a main lumen extending from the first tubular body portion to the second tubular body portion, the second tubular body portion having a smaller diameter than the first tubular body portion, the second tubular body portion having at least one aperture in a graft sidewall for receiving a side branch stent graft such that when the stent graft is in a curved state, the at least one aperture is located on or adjacent the outside of the curve, wherein the aperture opens into a recess and said recess extends proximally towards the first tubular body portion, wherein the recess comprises a volume of space bounded by the aperture in the graft sidewall and openings of at least two tubes which extend towards the proximal end of the stent graft, wherein proximal openings of the at least two tubes open directly in communication with the main lumen of the stent graft.

2. A stent graft for placement in the thoracic arch of a patient, the stent graft comprising a first tubular body portion, a second tubular body portion, and a main lumen extending from the first tubular body portion to the second tubular body portion, the second tubular body portion having a smaller diameter than the first tubular body portion, the second tubular body portion having at least one aperture in a graft sidewall for receiving a side branch stent graft such that when the stent graft is in a curved state, the at least one aperture is located on or adjacent the outside of the curve, wherein the aperture opens into a recess, wherein the recess comprises a volume of space bounded by the aperture in the graft sidewall and an opening of an internal tube, wherein the internal tube is divided along part of its length into at least two smaller internal tubes, and wherein proximal openings of the at least two smaller internal tubes open directly in communication with the main lumen of the stent graft.

3. A stent graft as claimed in claim 2 wherein the smaller internal tubes each have a diameter in the range of from 6 to 12 mm.

4. A stent graft as claimed in claim 2 wherein the smaller internal tubes each comprise stent reinforcement.

5. A stent graft as claimed in claim 2 wherein the two smaller internal tubes have diameters of 10 mm and 12 mm respectively.

6. A stent graft as claimed in claim 2 wherein one of the two smaller internal tubes has a diameter in the range of from 6 to 10 mm and the other of the two smaller internal tubes has a diameter in the range of from 8 to 12 mm.

7. A stent graft as claimed in claim 6 wherein a larger of the two smaller internal tubes is adjacent the wall of the first portion.

8. A stent graft as claimed in claim 2 wherein proximal ends of the smaller tubes are joined to each other.

9. A stent graft as claimed in claim 2 wherein at least a part of the smaller tubes are joined to a side wall of the first portion.

10. A stent graft for placement in the thoracic arch of a patient, the stent graft comprising a first tubular body portion, a second tubular body portion, and a main lumen extending from the first tubular body portion to the second tubular body portion, the second tubular body portion having a smaller diameter than the first tubular body portion, the second tubular body portion having at least one aperture in a graft sidewall for receiving a side branch stent graft such that when the stent graft is in a curved state, the at least one aperture is located on or adjacent the outside of the curve, wherein the aperture opens into a recess, wherein the recess comprises a volume of space bounded by the aperture in the graft sidewall and an opening of an internal tube, wherein the internal tube is divided into three smaller internal tubes extending towards the proximal end of the stent graft, and wherein proximal openings of the three smaller internal tubes open directly in communication with the main lumen of the stent graft.

* * * * *